United States Patent
Provost et al.

(10) Patent No.: US 6,892,393 B1
(45) Date of Patent: May 17, 2005

(54) SAFETY HELMET ATTACHMENT AND METHOD FOR SHIELDING EYES

(76) Inventors: Jack Provost, 17 Canterbury Rd., Chatham, NJ (US) 07928; Dennis Jenkins, P.O. Box 312, Denville, NJ (US) 07834

( * ) Notice: Subject to any disclaimer, the term of this patent is extended or adjusted under 35 U.S.C. 154(b) by 0 days.

(21) Appl. No.: 10/746,374

(22) Filed: Dec. 29, 2003

(51) Int. Cl.[7] .................................................. A61F 9/00
(52) U.S. Cl. ........................................................... 2/10
(58) Field of Search ............................ 2/10, 424, 452, 2/453, 422, 209.13; 351/155

(56) References Cited

U.S. PATENT DOCUMENTS

| | | | | |
|---|---|---|---|---|
| 857,838 A | * | 6/1907 | Shaw ........................... | 351/155 |
| 860,322 A | * | 7/1907 | Paroubek ....................... | 2/10 |
| 1,678,208 A | * | 7/1928 | Chambers ...................... | 2/453 |
| 1,916,678 A | * | 7/1933 | Malcom ............................ | 2/8 |
| 2,013,636 A | * | 9/1935 | Shoskey et al. ................. | 2/10 |
| 2,388,626 A | * | 11/1945 | Wilson .......................... | 2/453 |
| 2,725,560 A | * | 12/1955 | Feldman ......................... | 2/10 |
| 4,124,902 A | * | 11/1978 | Seres et al. ..................... | 2/10 |
| 4,752,974 A | * | 6/1988 | Haino ............................. | 2/424 |
| 4,856,089 A | * | 8/1989 | Horton ......................... | 455/351 |
| 5,012,528 A | * | 5/1991 | Pernicka et al. ................. | 2/10 |
| 5,252,069 A | * | 10/1993 | Lamb et al. ................... | 434/35 |
| 5,278,999 A | * | 1/1994 | Brown et al. ................... | 2/209 |
| 5,289,592 A | * | 3/1994 | Paivarinta ...................... | 2/431 |
| 5,533,207 A | * | 7/1996 | Diaz .............................. | 2/10 |
| 5,658,065 A | * | 8/1997 | Jamieson .................... | 362/106 |
| 5,669,071 A | * | 9/1997 | Vu .................................. | 2/10 |
| 5,720,040 A | * | 2/1998 | Simone .......................... | 2/10 |
| 5,907,868 A | * | 6/1999 | Schleger et al. ................. | 2/10 |
| 5,940,891 A | * | 8/1999 | Lane ............................. | 2/426 |
| 5,966,738 A | * | 10/1999 | Wang Lee ...................... | 2/10 |
| 6,595,635 B2 | * | 7/2003 | Schubert ..................... | 351/155 |

* cited by examiner

*Primary Examiner*—Rodney M. Lindsey
(74) *Attorney, Agent, or Firm*—Thomas L. Adams (57) ABSTRACT

An eye shield attachment can be used in combination with a safety helmet. The helmet has a front brim continuous with a rim extending along each opposite side of the safety helmet adjacent to a pair of rim slots in the rim of the safety helmet. The eye shield attachment has a lens and a right and a left structure. Each of the right and left structures has (a) a side frame adapted to be suspended below the rim and to extend toward the front brim, and (b) at least one tong adapted to be removably and dependently attached from below to a corresponding one of the rim slots in the helmet for supporting the side frame. The lens is attached distally between the right and the left structures and can pivot under the front brim between a lowered and a raised position and still remain subjacent to the front brim. The right and left structures are adjustable to provide an adjustable orientation of the lens while in the lowered position.

32 Claims, 6 Drawing Sheets

SAFETY HELMET ATTACHMENT AND METHOD FOR SHIELDING EYES

BACKGROUND OF THE INVENTION

1. Field of the Invention

The present invention relates to devices and methods for shielding the eyes, and in particular, to eye shields designed to attach to a safety helmet.

2. Description of Related Art

Construction workers and emergency personnel often wear safety helmets under varying conditions and for extended periods of time. The users of these helmets may also wear safety glasses for avoiding eye injury, or ordinary sunglasses to deal with bright light and glare. When doing close-up work or when working in a relatively dark environment, safety helmet users will often temporarily remove their glasses. The temporarily removed glasses are then often lost or damaged. In some cases a user may wish to glance at a bright scene or a dark scene and therefore may wish to briefly don or remove sunglasses, but this process is inconvenient and for efficiency's sake may be performed by temporarily lifting or removing the safety helmet. Obviously, helmet removal is to be avoided for safety reasons.

The safety helmets known as hardhats typically have right and left slots along the lower rim of the helmet for holding accessories such as ear muffs. See for example U.S. Pat. No. 4,639,950. In FIGS. 6 and 7 of U.S. Pat. No. 5,012,528 a visor 96 is attached through pivot 92 to arm 88, which connects through pivot 92 to a connecting member 86 that is attached to side slots on a hard hat from above. When not needed, visor 96 swings upwardly to a position above the brim of the hard hat. See also U.S. Pat. No. 4,479,738.

In U.S. Pat. No. 5,966,738 a safety visor is attached to an arm 21 that is pivotally connected to blocks 22 that are designed to snap into the side slots on a hard hat from above. The visor is positioned in front of the brim when in use. When no longer needed, the visor swings into a position above the brim. See also U.S. Pat. No. 4,442,551.

In U.S. Pat. No. 5,533,207 an eye shade 13 is bolted or screwed to bill 12 of a hard hat.

In FIG. 5 of U.S. Patent Application Publication No. U.S. 2002/0069489 a pair of wings 10 are clipped into the side slots of a hard hat to provide a nook for holding the temples of sunglasses that are not in use.

In U.S. Pat. No. 5,926,854 a face shield is hinged to a bracket that is screwed or bolted onto the side of a protective helmet.

In U.S. Pat. No. 6,490,729 the goggles straps 34 can be pushed onto quick fasteners that attach to the edge of a safety helmet.

See also U.S. Pat. No. 6,134,719 (helmet windshield attached to the helmet by pivots 11); U.S. Pat. No. 5,890,233 (alternative visors pivotally connected to the side of a light sports helmet); U.S. Pat. No. 4,856,109; and U.S. Pat. No. 6,185,739.

SUMMARY OF THE INVENTION

In accordance with the illustrative embodiments demonstrating features and advantages of the present invention, there is provided an eye shield attachment for use in combination with a safety helmet. The helmet has a front brim continuous with a rim extending along each opposite side of the safety helmet to a pair of rim slots in the rim of the safety helmet. The eye shield attachment has a right and a left structure each adapted to removably attach to a corresponding one of the rim slots in the helmet and extend along the rim to the front brim. Also included is a lens attached distally between the right and the left structures to pivot under the front brim between a lowered and a raised position and remain subjacent to the front brim.

In accordance with another aspect of the invention, an eye shield attachment is used in combination with the foregoing safety helmet. The eye shield attachment has a right and a left structure each adapted to removably attach to a corresponding one of the rim slots in the helmet and extend along the rim to the front brim. Also included is a lens attached distally between the right and the left structures to pivot between a lowered and a raised position. The right and left structures are adjustable to provide an adjustable orientation of the lens while in the lowered position.

In accordance with yet another aspect of the invention, an eye shield attachment is used in combination with the foregoing safety helmet. The eye shield attachment has a right and a left structure each with (a) a side frame adapted to be suspended below the rim and extend toward the front brim, and (b) at least one tong adapted to be removably and dependently attached from below to a corresponding one of the rim slots in the helmet for supporting the side frame. Also included is a lens attached distally between the side frames of the right and the left structures.

In accordance with still yet another aspect of the invention, a method is provided for attaching an eye shield to the foregoing safety helmet. The method includes the step of attaching to the pair of rim slots, support structure that extends along the rim to the front brim. Another step is moving the eye shield between a raised and a lowered position. The method also includes the step of adjusting the position of the eye shield while in the lowered position.

In accordance with still yet another aspect of the invention, a method is provided for attaching an eye shield to the foregoing safety helmet. The method includes the step of inserting into the rim slots from below, support structure that extends along the rim to the front brim. Another step is adjusting the position of the eye shield while under the front brim.

By employing apparatus and methods of the foregoing type, an improved eye shield attachment is achieved. In a preferred embodiment, a pair of hubs each have tongs that snap into rim slots on the sides of a conventional safety helmet. A pair of preferred telescopic temples project from these hubs so that their longitudinal and angular orientation can be adjusted. A lens is rotatably attached to the ends of the temples in order to flip up from a lower position to a raised position. The pivoting is arranged to allow the lens to flip up and still remain subjacent to the brim of the helmet.

Accordingly, the preferred eye shield attachment can be conveniently placed on a safety helmet and adjusted so that the lens is located below the brim of the helmet at a position that is in front of the user's eyes and spaced far enough away for comfort, including far enough away to accommodate a user's eyeglasses. The preferred lenses are attached to the temples by pivot pins. The pivot pins are easily removable so lenses can be replaced to provide different lenses with different tinting, etc. The preferred lenses extend back to provide lateral protection against eye injury.

BRIEF DESCRIPTION OF THE DRAWINGS

The above brief description as well as other objects, features and advantages of the present invention will be more fully appreciated by reference to the following detailed description of presently preferred but nonetheless illustrative embodiments in accordance with the present invention when taken in conjunction with the accompanying drawings, wherein.

DETAILED DESCRIPTION OF THE PREFERRED EMBODIMENTS

Figure 1:
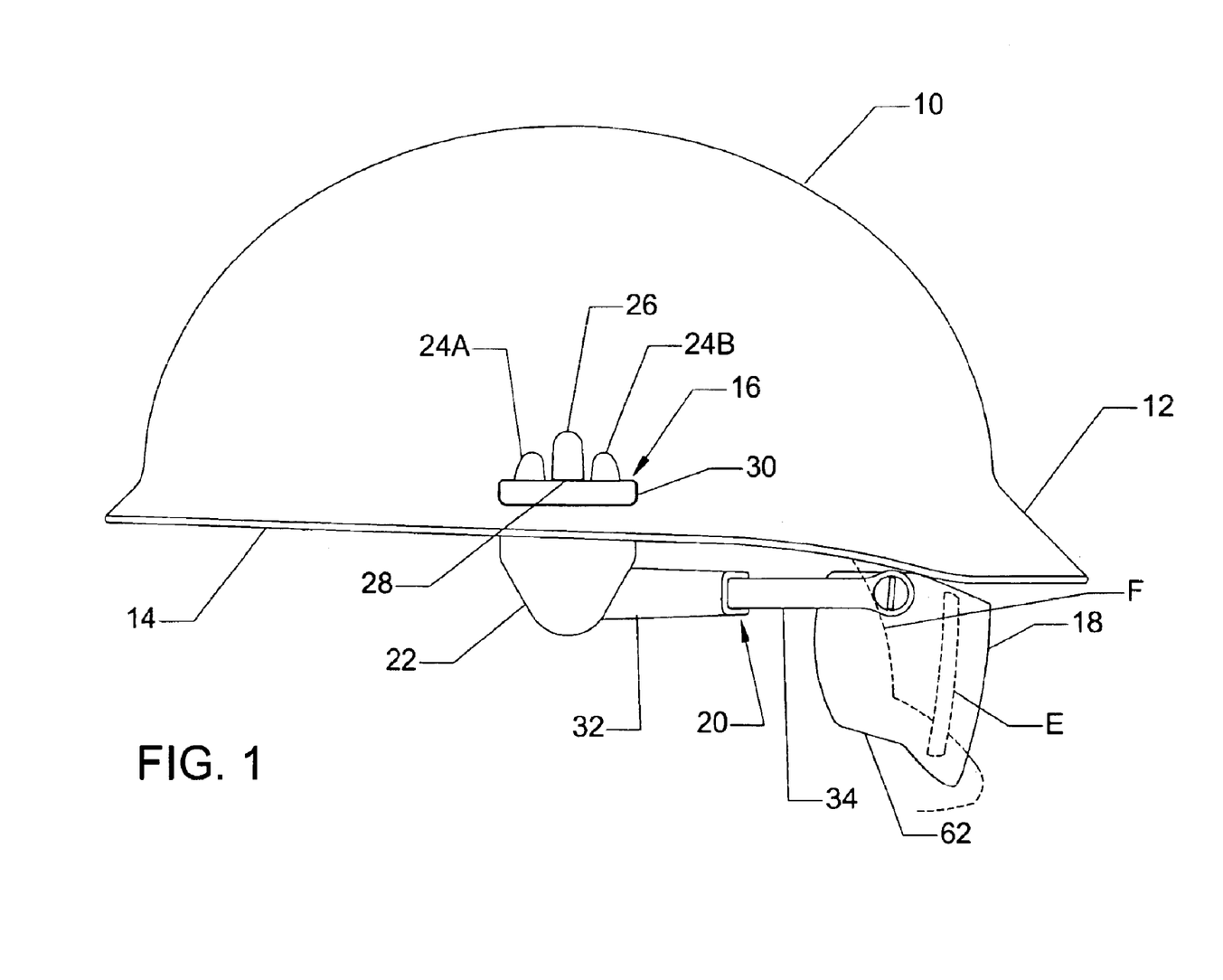
FIG. 1 is a perspective view of a safety helmet with an eye shield attachment in accordance with principles of the present invention.

Referring to FIG. 1 a safety helmet 10 is shown as a hard hat, although other safety helmets may be employed having different shapes, including the shape associated with the helmets worn by firefighters. The front brim 12 of helmet 10 is shown as a somewhat elongated bill, although embodiments are contemplated where the front brim of the helmet will simply be an edge without any substantial forward projection. Therefore, as used herein, the term brim does not necessarily imply an outwardly projecting element.

The rim 14 of helmet 10 extends continuously from front brim 12. The helmet 10 has on its right and left side along rim 14 a conventional rim slot 16 in the form of a four-sided rectangular passage open at its upper and lower ends.

An eye shield attachment is shown mounted in rim slot 16. In particular, a lens 18 is shown mounted distally, that is, on the distal end of a side frame 20. The proximal end of side frame 20 is pivotally attached to a hub 22. Side frame 20 and hub 22 taken together are herein referred to as a right structure. It will be appreciated that a mirror-image, left structure is attached to the other rim slot on the opposite side of helmet 10. Lens 18 is mounted distally on this right and left structure.

A pair of tongs 24A and 24B upwardly projecting from hub 22 are shown reaching out of the top of rim slot 16. A longer tong 26, also affixed to hub 22, upwardly projects between tongs 24A and 24B (the trio of tongs 24A, 24B, and 26 are also referred to as a plurality of tabs). Center tong 26 has a step or shoulder 28 designed to latch over the upper edge of the outside wall 30 of rim slot 16. As described further hereinafter, center tong 26 is deflectable to allow it to latch and unlatch in rim slot 16.

Referring to FIGS. 2, 3, 4 and 6, center tong 26 is shown being for the most part thinner than tongs 24A and 24B, except for the ramping shoulder portion 28, which is shown with a barbed or eave-like shape. The underside or undercut of shoulder 28 is designed to latch as described previously in connection with FIG. 1. Being thinner, tong 26 is more easily deflected so that shoulder 28 can retract for unlatching, or swing back for latching. The tong 26 is thinned by having an inside face that is set back relative to the back faces of tongs 24A and 24B, which also have thickening ribs 25A and 25B. The outside faces of tongs 24A, 24B, and 26 are substantially coplanar, except for the shoulder portion 28.

Accordingly, tongs 24A and 24B will center the assembly in the rim slot with tong 26 latching the assembly in place. Preferably, hub 22 and the tongs 24A, 24B, and 26 will be a single, integrally molded plastic item, although other embodiments may employ multiple components made of various materials.

Previously mentioned side frame 20 is shown with a channel 32 slidably supporting a telescopic temple 34. Channel 32 has for the most part a U-shaped cross-section forming a longitudinal groove receiving temple 34. The proximal end of channel 32 merges into a cylindrical stub 32A having coaxial hole 36. Temple 34 is embraced on three sides by channel 32, except where its bridge 37 forms an annular structure that encloses temple 34 on the fourth side. The rest of temple 34 in channel 32 is enclosed by a cover 44 that is held in place by screw 46 and by a tongue 43 designed to fit under bridge 37.

The distal end of stub 32A facing hub 22 fits over a cylindrical journal 48 formed on the inside face of hub 22. The outward face of stub 32A has a cylindrical recess 33 that is sized to receive journal 48. Recess 33 is inscribed on its inner circumference with five lower grooves or serrations 32B and five upper grooves or serrations 32C. Journal 48 has on its circumference at the 12 o'clock and 6 o'clock positions axial ribs 49 designed to snap into one of the grooves 32B and 32C. Preferably, channel 32 can be detained relative to hub 22 in a neutral position or to other detent positions that are reached by rotating channel 32 from neutral in either direction by two increments of 10° to 12° each to thereby adjust the angle of elevation of side frames 20.

Screw 46 is sized to pass through hole 45 in cover 44 and hole 36 in stub 32A and be screwed into the coaxial boss 51 of journal 48, while still allowing stub 32A to rotate relative to journal 48. The serrations 32B and 32C of stub 32A will act as detents as the ribs 49 ratchet against the serrations.

A rack of ridges or teeth 40 are located along a proximal portion of groove 38 of temple 34. A nub 41 on the tip of cantilever 42 can act as a detent that ratchets on successive ones of the teeth 40, as temple 34 slides telescopically in channel 32. Cantilever 42 is formed by molding cover 44 with a long U-shaped slot.

Figure 2:
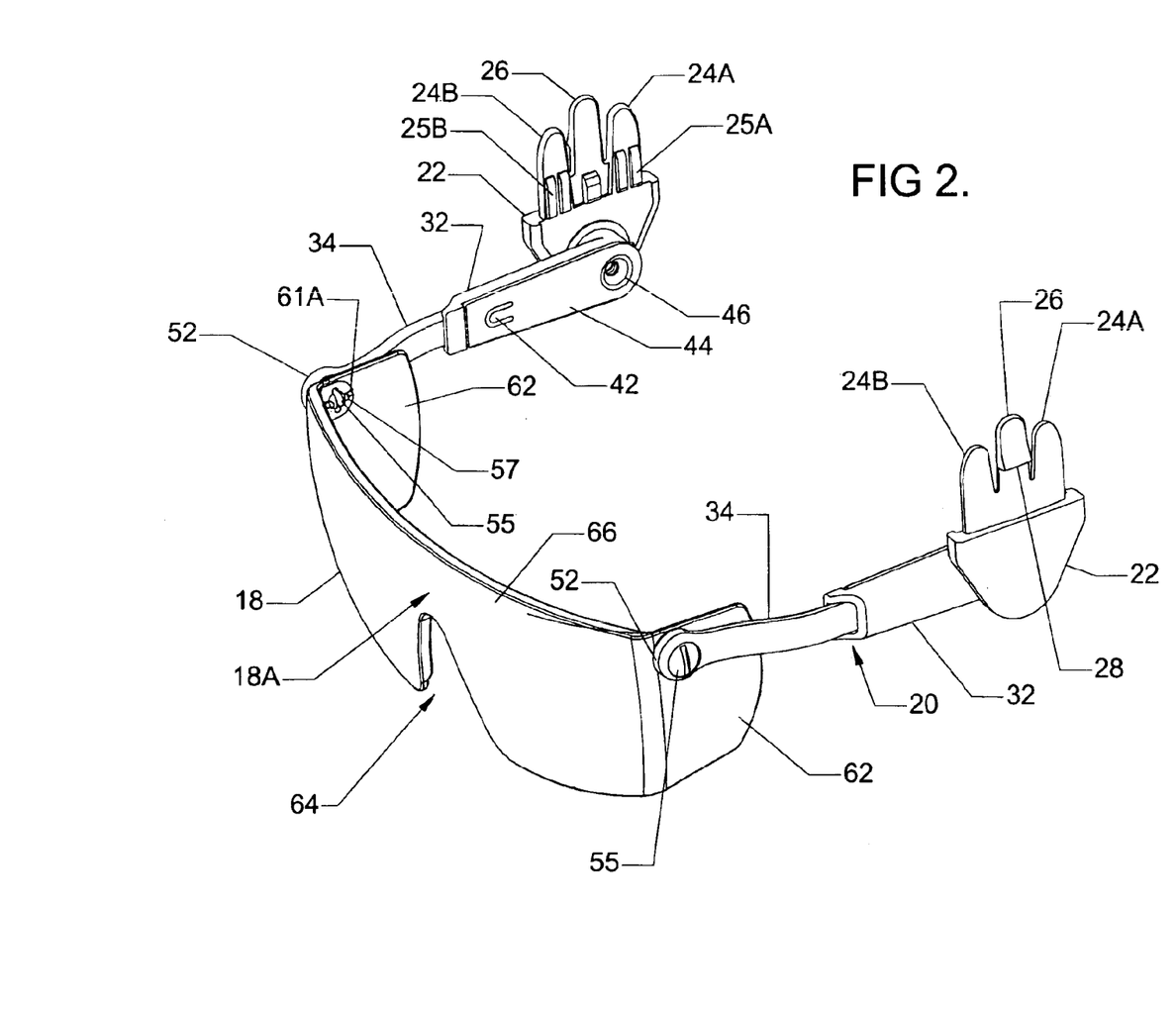
FIG. 2 is a separate, perspective view of the eye shield attachment of FIG. 1.
Figure 3:
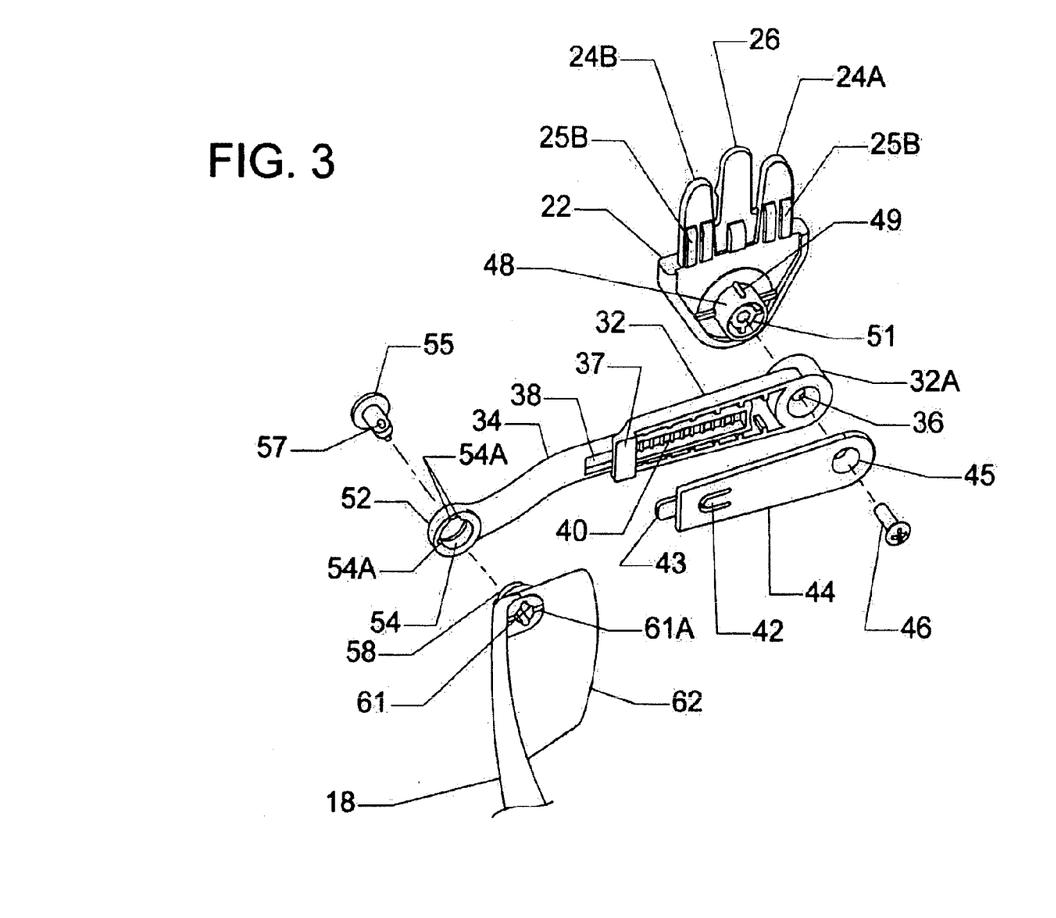
FIG. 3 is an exploded, perspective view of one of the side frames of the attachment of FIG. 2.
Figure 4:
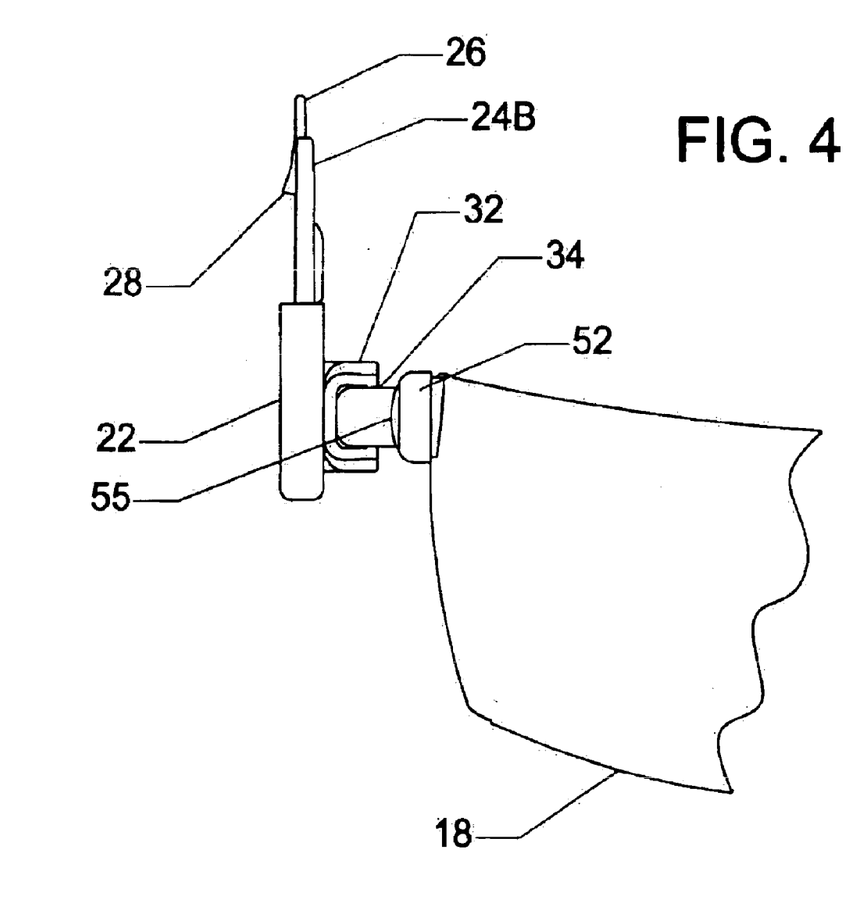
FIG. 4 is a detailed, fragmentary, front view of one of the joints of the attachment of FIG. 1.
Figure 6:
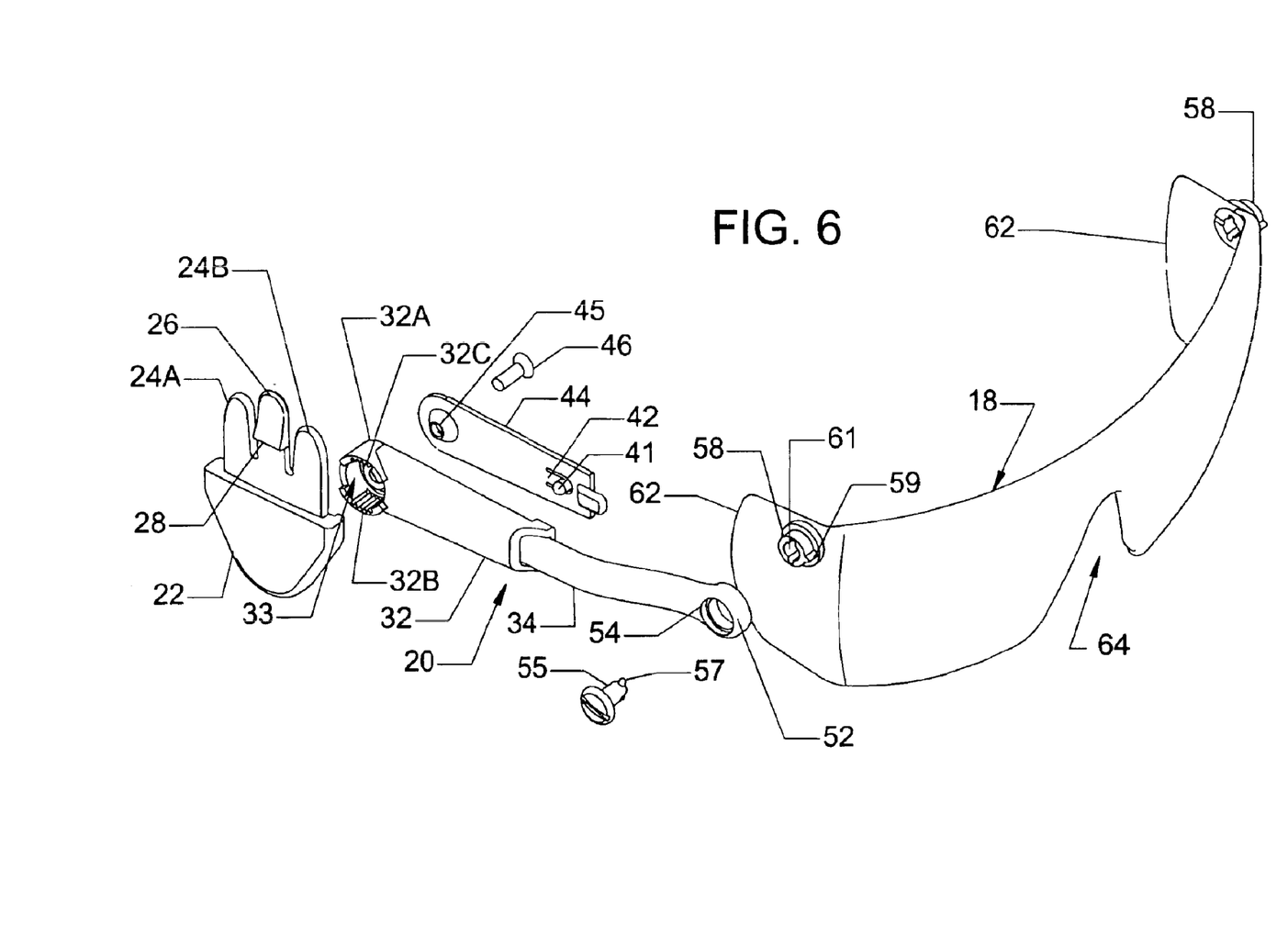
FIG. 6 is an exploded, perspective view of the lens and one of the side frames of the attachment of FIG. 1.

Temples 34 each have a central jog that brings their distal ends 52 closer together. The distal ends 52 are formed into enlarged heads that form an annular bearing 54. Lens 18 has on its upper corners a pair of hubs 58 that are journalled in annular bearings 54 to form a pivot joint th at pivotally supports lens 18. Bearing 54 is shown with axial grooves 54A at the 12 o'clock, 9 o'clock and 10:30 positions for detaining the lens 18 as it rotates to a lowered position (0°), intermediate position (75°), or a fully raised position (90°).

Lens 18 is locked in place with fastener 55 shown as a shaft having a slotted head on one end and on the opposite end a bifurcated tip fitted with an opposing pair of transverse nubs 57. The shaft and nubs 57 of fastener 55 can slide into the outside opening of a φ-shaped through-bore 61 in hub 58 and can reach an inside opening that communicates with a pair of transverse channels 61A. Accordingly, fastener 55 can be fully inserted into bore 61 with nubs 57 vertical before being given a quarter turn that causes nubs 57 to snap into channels 61A and lock lens 18 onto temple 34.

The front of lens 18 is convex so that the lens curves backwardly from front section 18A. The right and left portions of lens 18 are bent back into a pair of wings 62, designed to provide lateral protection against eye injury.

Suitably, the front to back length of wings 62 will be greater than 1 cm, and preferably greater than 2 cm. It is desirable to space the tips of wings 62 about 1–4 cm from a plane tangent to the outside surface of the front section 18A.

Figure 5:
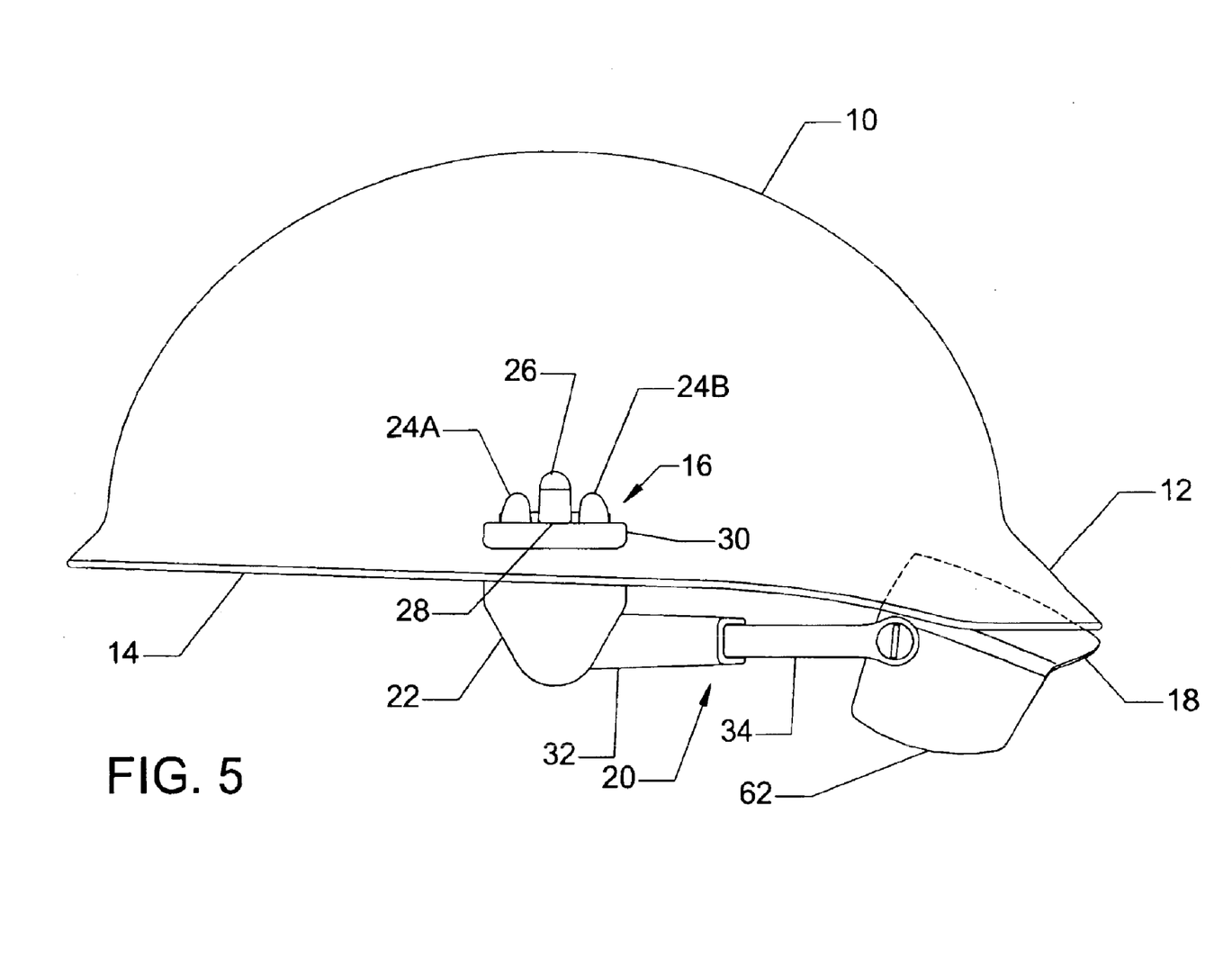
FIG. 5 is a side view of the eye shield attachment of FIG. 1 shown with its lens in a raised position.

The lower edge of lens 18 below the front section 18A has an indentation 64 designed to fit over a user's nose. The upper edge 66 of lens 18 is concave and is designed to conform to and provide clearance at a user's forehead when lens 18 is swung into the raised position shown in FIG. 5. It will be noticed that the pivot joint formed by hubs 58 create an effective horizontal axis of rotation below brim 12. Also, lens 18 swings from a lower into a raised position while still remaining at a position subjacent to the brim 12.

Lens 18 may be made of transparent plastic tinted to provide a degree of eye shading. Preferably, lens 18 can be removed from temples 34 by unfastening bearing 54 from journals 58. This allows a user to change the lens to an untinted clear lens when no eye shading is required but eye protection is still desired. Alternatively, the lens can be replaced to provide darker or lighter tints to suit the ambient light intensity. In addition, the tints can be selected to provide a different color to accommodate lighting conditions or simply for personal preferences or for reasons or fashion.

To facilitate an understanding of the principles associated with the foregoing apparatus, its operation will be briefly described. A user may select any one of the conventional safety helmets having rim slots similar to slot 16 of FIG. 1. The foregoing eye shield attachment may be installed by grasping one of the hubs 22 and inserting the tongs 24A, 24B, and 26 from below into the rim slot 16. The tongs 24A and 24B will guide and center the assembly. Tong 26 will deflect inwardly to accommodate the narrow clearance inside rim slot 16. When fully inserted, shoulder 28 will clear the upper edge of the wall 30 of rim slot 16 and snap into place to latch hub 22 onto the rim slot 16. The foregoing operation will be performed on the right and left side so that right and left structures 20 are held in place below rim 14 as shown in FIG. 1.

The user may now telescopically and longitudinally adjust temple 34 relative to channel 32. Preferably, lens 18 will be spaced from the user's face F (FIG. 1) to avoid pressure on the face or nose and thereby increase the wearing comfort. Moreover, the temple 34 can be extended to provide clearance for eyeglasses E that the user may be wearing. As temple 34 slides inside channel 32 nub 41 of cantilever 42 will ratchet over the teeth 40 formed in the groove 38 of temple 34 to thereby provide a number of successive detent positions.

In addition, the user may elevationally adjust lens 18 by adjusting the angle of elevation of side frame 20. This adjustment allows the user to vertically center lens 18 relative to the user's eyes, as well as provide an appropriate clearance from the underside of front brim 12. Once angularly adjusted, side frames will tend to stay in the same angular orientation since the serrations 32B and 32C (FIG. 6) in stub 32A will engage the ribs 49 (FIG. 3) on journal 48 of hub 22.

When the user is wearing the helmet 10 lens 18 will typically be positioned as shown in FIG. 1 providing protection for the user's eyes and, if desired, shading. If there is some need to get the lens 18 away from the user's eyes, the lens 18 can be quickly flipped up to the raised position shown in FIG. 5. The illustrated raised position is the 75° position offered by the intermediate one of the grooves 54A (FIG. 3). This process can be performed without removing helmet 10. Because upper edge 66 is concave there will be clearance between the lens 18 and the user's forehead when the lens is in the raised position.

Also, since the lens 18 is stored in the raised position by side frame 20, the lens will not be lost or damaged. Furthermore, the lens 18 can be quickly flipped back to the operative position again without the need to remove helmet 10.

In some embodiments bearing 58 will be non-symmetrical and have an inward lobe that can snap into a matching indentation in journal 58. This feature will also allow the lens to be swung upwardly and detained in the raised position. Alternatively, no detents will be provided and the rotating joints at the distal and proximal ends of side structures 20 will have a friction fit that allows continuous angular adjustment. Similarly, temple 32 may have a frictional telescopic joint that allows continuous longitudinal adjustment.

It is appreciated that various modifications may be implemented with respect to the above described, preferred embodiments. For example, the outline, shape, and curvature of the lens can be adjusted to accommodate various helmets, users' head sizes, personal preferences, fashion considerations, etc. In some cases, the lens will be given a curvature to act as prescription lenses that correct the user's sight deficiencies. Furthermore, the pivot point of the lens can be repositioned to alter the height reached by the lens when swung into the raised position. Moreover, some embodiments may have a brace spanning the distal ends of the side frames and the lens may be pivotally mounted on that brace. In some embodiments a ball will be formed at the distal end of the side frames that will snap into sockets on the lens or vice versa. In still other embodiments, the ball joint may be replaced with a simple hinge, including a live hinge. Also, in some embodiments the side frames may be made of a flexible material that can be arbitrarily bent to adjust the position of the lens. In addition, instead of telescopic side frames, some embodiments will allow the lens to slide on a rail or groove in the side frames. Also, instead of a plurality of tongs, the eye shield attachment may have a removable component that is inserted down through the rim slot to attach to structure located below the rim of the helmet that ultimately supports the lens. Moreover, instead of a central tong that latches by deflecting in and out, a pair of side tongs may flex together, front to back. Still other embodiments may use a hook-like structure that is inserted down into the rim slot but with an external structure that extends downwardly on the outside of the helmet to a position below the helmet rim to support a side frame below the helmet rim.

Obviously, many modifications and variations of the present invention are possible in light of the above teachings. It is therefore to be understood that within the scope of the appended claims, the invention may be practiced otherwise than as specifically described.

What is claimed is:

1. An eye shield attachment for use in combination with a safety helmet having a front brim continuous with a rim extending along each opposite side of said safety helmet to a pair of rim slots in the rim of said safety helmet, said eye shield attachment comprising:

a right and a left structure each adapted to removably attach to a corresponding one of said rim slots in said helmet and extend along said rim to said front brim; and a lens attached distally between said right and said left structures to pivot under said front brim between a lowered and a raised position about an axis supported by said rim slots, the axis remaining (a) closer to said front brim than to said rim slots, and (b) lower than said front brim to keep said lens subjacent to said front brim, in said raised position said lens being below and facing upwardly toward said brim.

2. An eye shield attachment according to claim 1 wherein said lens is removable from said right and said left structure so that said lens can be replaced.

3. An eye shield attachment according to claim 1 wherein said lens has a concave upper edge curved to provide in said raised position clearance for a user's forehead.

4. An eye shield attachment according to claim 1 wherein said right and said left structure are adjustable to provide an adjustable orientation of said lens while in said lowered position.

5. An eye shield attachment according to claim 4 wherein said right and left structure are elevationally adjustable.

6. An eye shield attachment according to claim 5 wherein said right and left structure each have an adjustable angle of elevation.

7. An eye shield attachment according to claim 1 wherein the lens has a forwardmost section between a right and left section, said right and left section each being rearwardly spaced from said forwardmost section by 1 to 4 cm.

8. An eye shield attachment according to claim 4 wherein said right and left structure are longitudinally adjustable.

9. An eye shield attachment according to claim 8 wherein said right and left structure are adjustable to provide adjustable clearance to avoid contacting a user's face with said lens.

10. An eye shield attachment according to claim 8 wherein said right and left structure are adjustable to provide adjustable clearance to accommodate users with or without eyeglasses.

11. An eye shield attachment according to claim 8 wherein said right and left structure are telescopically adjustable.

12. An eye shield attachment according to claim 1 wherein said right and said left structure each have (a) a side frame adapted to be suspended below said rim and extend toward said front brim, and (b) at least one tong adapted to be removably and dependently attached from below to a corresponding one of said rim slots in said helmet for supporting said side frame.

13. An eye shield attachment according to claim 12 wherein said at least one tong comprises a plurality of tabs, one of them being deflectable and having a shoulder sized to pass through and lock onto said rim slot.

14. An eye shield attachment according to claim 1 wherein said lens has a front section and a right and a left rearwardly extending wing sized to provide lateral eye protection.

15. An eye shield attachment according to claim 14 wherein said right and said left wing each extend rearwardly at least 1 cm.

16. An eye shield attachment according to claim 14 wherein said right and said left wing each extend rearwardly at least 2 cm.

17. A method for attaching an eye shield to a safety helmet having a front brim continuous with a rim extending along each opposite side of said safety helmet to a pair of rim slots in the rim of said safety helmet, the method comprising the steps of:
   inserting into said rim slots from below, support structure that extends along said rim to said front brim; and
   adjusting the position of said eye shield while under said front brim.

18. An eye shield attachment for use in combination with a safety helmet having a front brim continuous with a rim extending along each opposite side of said safety helmet to a pair of rim slots in the rim of said safety helmet, said eye shield attachment comprising:
   a right and a left structure each adapted to removably attach to a corresponding one of said rim slots in said helmet and extend along said rim to said front brim; and
   a lens attached distally between said right and said left structures to pivot between a lowered and a raised position, in said raised position said lens being below and facing upwardly toward said brim, said right and left structure being adjustable while said lens is in said lowered position to provide an adjustable orientation of said lens through a movement that is different than that occurring for motion between said raised position and said lowered position.

19. An eye shield attachment according to claim 18 wherein said right and left structure are elevationally adjustable.

20. An eye shield attachment according to claim 19 wherein said right and left structure each have an adjustable angle of elevation.

21. An eye shield attachment according to claim 18 wherein said right and left structure are longitudinally adjustable.

22. An eye shield attachment according to claim 21 wherein said right and left structure are adjustable to provide adjustable clearance to avoid contacting a user's face with said lens.

23. An eye shield attachment according to claim 21 wherein said right and left structure are adjustable to provide adjustable clearance to accommodate users with or without eyeglasses.

24. An eye shield attachment according to claim 21 wherein said right and left structure are telescopically adjustable.

25. An eye shield attachment for use in combination with a safety helmet having a front brim continuous with a rim extending along each opposite side of said safety helmet to a pair of rim slots in the rim of said safety helmet, said eye shield attachment comprising:
   a right and a left structure each having (a) a side frame adapted to be suspended below said rim and extend toward said front brim, and (b) at least one tong adapted to be removably and dependently attached from below to a corresponding one of said rim slots in said helmet for supporting said side frame; and
   a lens attached distally between the side frames of said right and said left structures.

26. An eye shield attachment according to claim 25 wherein said at least one tong comprises a plurality of tabs, one of them being deflectable and having a shoulder sized to pass through and lock onto said rim slot.

27. A method for attaching an eye shield to a safety helmet having a front brim continuous with a rim extending along each opposite side of said safety helmet to a pair of rim slots in the rim of said safety helmet, the method comprising the steps of:
   attaching to said pair of rim slots, support structure that extends along said rim to said front brim;
   moving said eye shield between a raised and a lowered position, in said raised position said eye shield being below and facing upwardly toward said brim; and
   adjusting the position of said eye shield while in said lowered position with a motion different than that occurring when moving said eye shield between the raised and the lowered position.

28. A method according to claim 27 wherein the step of moving said eye shield between a raised and lowered position is performed with said eye shield remaining lower than said front brim.

29. A method according to claim 27 wherein the step of adjusting said eye shield while lowered is performed by moving said eye shield toward and away from a user's face, so that eyeglasses are accommodated and the eye shield need not touch the user's face.

30. A method according to claim 29 wherein the step of adjusting said eye shield while lowered is performed by moving said eye shield elevationally.

31. A method according to claim 27 wherein the step of attaching the support structure is performed by insertion into said rim slots from below.

32. A method according to claim 27 comprising the step of:

replacing said eye shield with one having a different characteristic.

* * * * *